United States Patent [19]

Péault

[11] Patent Number: 5,538,713

[45] Date of Patent: Jul. 23, 1996

[54] PRIMORDIAL IMPLANTS IN IMMUNODEFICIENT HOSTS

[75] Inventor: Bruno Péault, Menlo Park, Calif.

[73] Assignee: Systemix, Inc., Palo Alto, Calif.

[21] Appl. No.: 462,766

[22] Filed: Jun. 5, 1995

Related U.S. Application Data

[63] Continuation of Ser. No. 740,000, Aug. 2, 1991, abandoned.

[51] Int. Cl.$^6$ ............................................. A61K 49/00
[52] U.S. Cl. .................. 424/9.2; 424/549; 424/582; 424/577; 424/557; 424/937; 800/2; 800/DIG. 5
[58] Field of Search ........................... 424/2, 9.2, 93.7, 424/549, 557, 577, 582; 800/2, DIG. 5

[56] References Cited

PUBLICATIONS

Groseworth et al., Anat. Embryol. 165:291–302 (1982).
Usadel et al., The Lancet, Feb. 12, 1977, p. 365.
Bastert et al., Endo. 101(2):365–368 (1977).
H. Fiebig, et al. (1987) Eur. J. Clin. Oncol. 23:937–948. Colony assay with human tumor xenografts, murine tumors and human bone marrow.
R. Taetle, et al. (1986) Cancer 58:1969–1978. Use of nude mouse xenografts as preclinical drug screens.
A. Drugan et al. (1989) Am. J. Obstet. Gyn. 160:289–293. Fetal organ and xenograft transplantation.
I. Moll, et al. (1990) J. Invest. Derm. 94:359–364. Intraepidermal formation of Merkel cells in xenografts of human fetal skin.
K. Elias, et al. (1990) Tranplant. Proc. 22:806–807. Development of human fetal xenograft transplants in diabetic nude mice.
R. Namikawa, et al. (1990) J. Exp. Med. 172:1055–1063. Long–term human hematopoiesis in the SCID–hu mouse.
H. Winter, et al. (1991) Gastroenterology 100:89–98. Human intestine matures as nude mouse xenograft.
D. Mosier (1991) Adv. Immunol. 50:303–325. Adoptive transfer of human lymphoid cells to severely immunodeficient mice: models for normal human immune function, autoimmunity, lymphomagenesis, and AIDS.
J. Fleischmann, et al. (1985) J. Urol. 134:570–574. Human renal cell carcinoma xenograft: morphology, growth and chemosensitivities.
J. Bennet, et al. (1986) J. Surg. Oncol. 33:8–13. Accurate prediction of experimental canver chemosensitivity using the subrenal capsule xenograft assay.
McCune et al., Science 241:1632–1639 (1988).
Poulsen et al., Nature 248:247–249 (1974).
Bosma et al., Nature 301:527–530 (1983).
Fulop et al., J. Immunology 136(12):4438–4443 (1986).

*Primary Examiner*—Jasemine C. Chambers
*Attorney, Agent, or Firm*—Bertram I. Rowland; Pamela J. Sherwood

[57] ABSTRACT

Primordial tissue is introduced into immunodeficient hosts, where the primordial tissue develops and differentiates. The chimeric host allows for investigation of the processes and development of the xenogeneic tissue, testing for the effects of various agents on the growth and differentiation of the tissue, as well as identification of agents involved with the growth and differentiation.

9 Claims, No Drawings

PRIMORDIAL IMPLANTS IN IMMUNODEFICIENT HOSTS

This is a continuation of application Ser. No. 07/740,000 filed Aug. 2, 1991, now abandoned.

TECHNICAL FIELD

The field of this invention is chimeric animals and their use in the study of developmental and physiological processes.

BACKGROUND

One of the problems in understanding human biological processes is the inability to study the processes in humans. For the most part, studies have had to be made on animals or mammals and the information obtained extrapolated to humans. In many situations, the animals used as surrogates are adequate to varying degrees.

Recently, the introduction of human fetal tissue into scid/scid mice has been reported, where thymus, lymph node and fetal liver have been introduced into the mouse to provide for various aspects of a human immune system in the mouse. These chimeric mice have found use in studying of HIV infection and the ability of drugs to counteract the infection. The chimeric animals therefore offer potential new opportunities for investigating various processes associated with human physiology and pathology.

SUMMARY OF THE INVENTION

Human tissue rudiments are introduced into internal sites of immunocompromised mammals, which site allows for vascularization of the rudiment. The rudiments are found to demonstrate growth, resulting in structures simulating natural development. Particularly, protochondral tissue is shown to develop into normally shaped bone. The developed organ may then be modified or processed and/or used for testing of agents. The effect of agents on the developing of the organ may be determined during development.

DESCRIPTION OF THE SPECIFIC EMBODIMENTS

It has now been found that primordia from fetuses, particularly human fetuses, generally of less than about 12 gestational weeks, can be introduced into an immunodeficient mammalian host at a site where vascularization can occur, and the tissue is found to mature with cell differentiation and proliferation, up to producing an organ having approximately or even the same structure and shape associated with a fetal organ of about the same age.

The tissue or organ primordia that are of particular interest include bone, lung buds, lymph node, thymus, nephros, stomach, heart, colon, nervous system, liver, spleen, gall blader, reproductive tract, etc. Of particular interest are bones where rudiments may be obtained from long bone anlages, e.g., tibia, femur, humerus, radius (ulna), etc., or other bones, such as skull, ribs and vertebrae. The primordia will generally be from 6 to 12 weeks, preferably 8 to 10 weeks gestational age.

Using bone as illustrative of other primordia, a long bone anlage is dissected under a microscope with microsurgery instruments, i.e., Pascheff-Wolff microscissors and fine forceps. Protochondral tissue is separated from surrounding mesenchyme, care being taken to extirpate the presumptive areas of both diaphyseal and epiphyseal areas. The primordium is then ready for implantation. The explant may then be transplanted into any convenient immunodeficient host.

The general principle is that the embryonic territory enclosing the whole presumptive region is dissected. With lung, the lung bud is an epithelial bag in the thoracic cavity at 8.5 g.w. This bag is dissected for implanting into the host. Similarly, other primordia may be dissected and implanted into an appropriate site.

A wide variety of immunodeficient hosts exist in various non-human mammals, such as primate, bovine, ovine, murine, feline, porcine, equine, canine, lagomorpha, and the like. Similarly, the xenogeneic tissue to be implanted in the host may come from any source as listed above, including human, which is the preferred source.

The primordial tissue may be introduced at any site which allows for vascularization, and as appropriate, lymphatic vessel connection. Depending upon the nature of the tissue and the size to which it grows, one site may be preferable over another. Since substantial growth is anticipated, preferred sites will include the kidney capsule, subcutaneous, peritoneum, mammary fat pad, cervical region, spleen and the like. The size of the tissue which is introduced will generally be greater than about 1 mm and less than about 8 mm, usually less than about 5 mm.

Single tissue may be introduced, or combinations of tissue, where only one of the tissue need be primordial. Thus, other fetal tissue which may be introduced having greater maturity than about 10 gestational weeks, usually ranging from about 12 to 36 gestational weeks, may include a wide variety of organs, such as lymph node, spleen, pancreas, gut, skin, lung and the like. These organs may be introduced at any one of the sites indicated above, as well as other sites, such as the popliteal fossa.

The non-primordial tissue may be fresh normal tissue, obtained within about 48 hrs of death, or freshly frozen tissue, tissue frozen within about 12 hrs of death and maintained at below about $-10°$ C., usually at about liquid nitrogen temperature ($-196°$ C.), where the tissue may be maintained substantially indefinitely. The tissue may be from an organ implanted in the chimeric host, where the tissue may be removed from 2 to 4 weeks after implantation, or longer. In this manner, the tissue originally obtained from the host source may be greatly expanded, substantially increasing the total number of chimeric hosts which may be obtained. The tissue obtained from the chimeric host may be treated analogously to the tissue obtained form the original tissue source host. The tissue may be provided as individual cells freed of attached stromal elements, as a dispersion, or as small tissue slices, generally of from about 0.5 mm to 4 mm, more usually from about 1 mm to 2 mm, generally of a thickness in the range of about 1 to 2 mm, so that the sections can easily fit into a trocar used for implantation, usually conveniently of about 15- to 20-gauge. Normally, the cells will not have been subject to culture in vitro for any extended period of time, e.g., three days or greater; for special purposes, however, such pre-implantation culture in vitro may prove desirable. In some cases, whole organ grafts may be transplanted by anastomosing donor and host blood vessels, lymphatic vessels, and other vessels such as ureters, etc. At certain sites, e.g., popliteal fossa and cervical region, lymphatic connection may be obtained.

In conjunction with certain tissues, such as bone, thymus or other lymphoid organ, it may be of interest to employ dispersed cells, where the relevant organs are teased apart to yield viable cells in suspension. Desirably, the suspension cells may be enriched with the particular cells of interest.

For example, with fetal liver cells, the suspension cells may be enriched for hematopoietic precursors by Ficoll-Hypaque density gradient centrifugation. Cells may also be enriched by other techniques, such as fluorescence-activated cell sorting, panning, magnetic bead separation, elutriation within a centrifugal field, or rosetting.

In some instances, it may be desirable to enrich cells by killing or removing other cells. This may be achieved by employing monoclonal antibodies specific for the undesired cells in the presence of complement or linked to a cytotoxic agent, such as a toxin, e.g., ricin, abrin, diphtheria toxin, or a radiolabel, e.g., $^{131}$I, or the like. Immunoaffinity columns may be employed, which allow for specific separation of either the desired or undesired cells, depending upon the nature of the mixture.

For various organs, irradiation may be used prior to or after implantation to kill cells, mutagenize cells, or the like. In addition, it may be desirable to irradiate all or a portion of the host for the same or different purpose. For example, with a scid/scid mouse, one may irradiate the mouse, particularly the long bones, with under about 400 rad, usually 150 to 250 rad. Bone primordia implants may be irradiated at 150 to 250 rads, prior to or subsequent to implantation. Other primordia mY also be similarly irradiated.

The recipient mammalian host may be subject to a variety of immune defects. Of particular interest is the defect resulting in non-functional T- and B-cells. Such dysfunction may-be achieved in SCID (severe combined immunodeficiency) animals. Current scid/scid species include mice, horses, and man. In the future, e.g., using transgenic cell-depletion techniques, SCID animals of other species may be developed. Other malfunctions may include non-functional stem cells, lack of surface membrane proteins associated with T-cell and B-cell function, incompetent receptors, e.g., T-cell receptor and surface immunoglobulin receptor, deficiency in T-cell and B-cell maturation, deficiency in natural killer cell activity, and nonfunctional thymic, lymph node, splenic or bone marrow stroma.

Besides the phenotypic deficiency, further reduction in immunocompetence may be achieved by irradiation of the host, or use of immunocytotoxic labels as indicated previously, e.g., antibodies specific for cells of the lymphoid (including natural killer cells) or myelomonocytic lineages. Particularly, where immunocompetence may be provided by the tissue introduced into the host, native immunocompetence can be enhanced above the low level naturally present in the particular phenotype of the host.

In appropriate situations, one or more organs may be removed for particular purposes. For example, a splenectomy may be performed to provide longer-term reconstitution of circulating red and other hematopoietic cells. Other organs may be removed for introduction and study of a xenogeneic organ. Bone marrow may be removed or destroyed by selective irradiation for introduction of xenogeneic bone marrow. Host stromal cells may be removed to provide xenogeneic stromal cells for a more natural environment for xenogeneic stem cells.

The host will usually be of an age less than about 25% of the normal lifetime of an immunocompetent host, usually about 1 to 20% of the normal lifetime. Generally, the host will be at least about 3 weeks old and large enough to manipulate for introduction of the donor mammalian cells at the desired site. For example, mice which may be considered to have about a 2–4 year lifetime are used at about 3 to 10, usually 4 to 8 weeks, of age. Growth of the tissue within the host will vary with the organ, usually being at least a 5-fold, more usually at least a 10-fold and may be a 100-fold or more increase in size (volume).

Depending upon the tissue which is introduced into the host, the nature of the host, and the combinations of tissue employed, various results can be achieved. Of particular interest in the hematopoietic system is the production of sets and subsets of cells, particularly T-cells and/or B-cells. For example, by using fetal liver stem cells in conjunction with a thymus from the same species or host (allogeneic or syngeneic) in the immunocompromised host, T-cells, B-cells, and myelomonocytic cells can be produced which are native to the source host. The production of the T-cells, as well as any other source host cells, may be enhanced by introducing various lymphokines, cytokines, and growth factors from the tissue host source into the mammalian host. In this way, the growth of the desired cells may be further enhanced. Illustrative factors include each of the interleukins 1–1-1, particularly IL-1, -2, -3, -6 and -7; M-, G-, and GM-colony stimulating factor, interferons-$\alpha$, -$\beta$, and -$\gamma$, monokines, growth factors, etc. The amount that may be added will vary depending upon the nature of the mammalian host, the nature of the cell, as well as the nature of the factor.

The time for growing the tissue in vivo, will be at least one month, usually two months, preferably at least three months. Depending upon the nature of the tissue, it may be subject to treatment with various agents during the process of growth and maturation. For example, with bone, it is found that the bone grows to a size in excess of 2 cm, generally in excess of 3 cm, and may be 4 cm or greater depending upon the length of time the bone is allowed to grow, the survival of the host, as well as the size of the host and the location of the implant. With bone, it is observed that there is both bone and cartilage in their expected location, a normal trabeculated cavity is found in the shaft, and red hematopoietic marrow is found inside the bone graft, but appears to be primarily of mouse origin. Transverse sections of the graft reveal by histologic analysis the normal distribution of tissues including cartilage, calcified cartilage and bone.

The bone may be implanted with hematopoietic cells, e.g., bone marrow, of the same host species as the source of the bone. Desirably, the implanted bone may be irradiated prior to implanting the hematopoietic cells into the bone. In this manner, one may provide for fetal or adult bone marrow or fraction thereof, e.g., hematopoietic stem cells, to be introduced into the bone marrow shaft. One may also provide for stromal cells or stromal cell fractions, to support the growth of hematopoietic cells.

For bone, as well as other tissues, one can devise strategies for identifying processes associated with maturation and differentiation of tissue, identification of the formation of specific structures within tissue, e.g., cortex and medulla of thymus, etc., identify growth factors, either enhancing or inhibiting growth, investigate tumor metastases. One may also identify the effect of various compounds on the maturation and differentiation of the tissue and the ability for antagonists to prevent modulation of the tissue. In addition, one may be able to identify specific compounds, secreted, cytoplasmic, or surface membrane proteins, associated with the maturation and differentiation of the various tissues.

The mammalian host will be grown in conventional ways. Depending upon the degree of immunocompromised status of the mammalian host, the mammalian host may be protected to varying degrees from infection. Thus, in some instances, a sterile environment or prophylactic antibiosis may be indicated. Prophylactic antibiosis may be achieved for SCID mice with 25–75 mg trimethoprim and 100–300 mg sulfamethoxazole in 5 ml of suspension, given 3 days each week. Alternatively, it may be satisfactory to isolate the potential xenogeneic hosts from other animals in germ-free environments after caesarean derivation. The feeding and maintenance of the chimeric host will for the most part follow conventional techniques.

The foreign cells will usually be present for at least two weeks, usually at least four weeks and may be continuously present over periods of three months or more. For the most part, normal cells, tissue, and/or organs may be stably maintained and function for at least three to six months, frequently, at least 10 months.

The foreign cells are capable of remaining viable in the immunocompetent host and will be capable of functioning in the source host and frequently capable of functioning in the xenogeneic host. That is, besides carrying on normal metabolic processes, the cells will respond to ligands, transduce signals, secrete appropriate products and carry on normal functions as carried on by syngeneic or congeneic cells in their wild-type host. Furthermore, where organs are involved, the cells will define a tissue mass with appropriate architecture for the organ function.

The immunocompromised host may be used in a variety of ways associated with its ability to provide an environment in which stem cells may proliferate and differentiate. Thus, the host may be employed to detect the presence of stem cells in a cellular composition, which may be homogeneous or heterogeneous. A cellular composition, such as bone marrow, may be separated into fractions using, for example, a fluorescence-activated cell sorter (FACS). The fractions may then be injected intravascularly into the host. After sufficient time for the cells to differentiate, tissue or blood may be removed from the host to serve as a source of peripheral blood lymphocytes or other hematopoietic cell, e.g., erythroid, myeloid and platelets. If necessary, the stem cells could be MHC typed to ensure that the mature cells originate from the stem cells, with the stem cells having different MHC antigens from other hematopoietic cells which may be present in the host. The presence of mature cells of the various hematopoietic lineages would be indicative of progenitor cells, while the presence of all lineages would be indicative of stem cells. Again, the FACS could be used with advantage to determine the cellular population.

The following examples are offered by way of illustration and not by way of limitation.

EXPERIMENTAL

Materials and Methods

1. Materials

Whole human embryos are obtained from elective abortions performed after 6–12 weeks of gestation. CB-17 scid/scid mice aged 1 to 3 months are obtained from the SyStemix animal production facility.

2. Isolation of Tissue from Human Embryos

Long bone anlages (tibia, femur, humerus, ulna) are dissected under a microscope with microsurgery instruments, i.e., Passcheff-Wolff microscissors and fine forceps: protochondral tissue is separated from surrounding mesenchyme, care being taken to extirpate the presumptive areas of both diaphyseal and epiphyseal areas. In some experiments, rudiments (anlage) of other bones like skull, ribs and vertebrae are also harvested. Organ primordia that can be easily dissected out include lung buds, thymus, nephros, stomach, etc.

3. Transplantation of Human Tissue Rudiments into SCID Mice

Embryonic human bone anlage are transplanted under the kidney capsule of Nembutal-anesthetized SCID mice. Because of the small size of the implants, engraftment is performed under a dissecting microscope with the help of microsurgery instruments.

4. Evaluation of Human Fetal Grafts

At intervals, mice are sacrificed by cervical dislocation and human grafts are harvested. With bones, part of the graft is fixed, decalcified and processed for histologic analysis. When appropriate, one half of the bone is used for cytofluorometric analysis of the marrow cell population. For that purpose, the graft is crushed and marrow cells are dispersed mechanically by strong pipetting in appropriate medium.

Results

Human embryonic protochondral tissue was observed to undergo considerable growth upon transplantation in the SCID mouse. The femur anlage of a 10-week embryo (about 3–5 mm) reached a length of 4.5 cm after sojourning 6 months in the SCID mouse, exhibiting an essentially normal shape including developed diaphysis and epiphysis. Gross observation revealed the presence of both bone and cartilage in their expected locations, i.e., in the shaft and joint regions, respectively. Inside the shaft, a normal, trabeculated cavity was found. The red hematopoietic marrow found inside the bone graft was shown to be mostly of mouse host origin. The histologic analysis of transverse sections of the graft revealed the normal distribution of tissues including cartilage, calcified cartilage and bone. In conclusion, the graft which was only one-third smaller than an age-matched fetal femur exhibited the normal anatomical features of a long bone. Both differentiation, including calcification, and extensive growth of the human embryonic bone rudiment occurred in the SCID mouse and a long bone pattern was maintained. Similar observations were done on the growth of other human bone primordia such as vertebrae and ribs.

Lung bud was removed from the thoracic cavity of a fetus of about 8.5 gm and implanted in the kidney capsule. After about 2 months, the lung tissue had substantially grown approximating the size of the mouse kidney. The lung tissue had the typical spongy appearance and folding of human fetal lung tissue of comparable age.

It is evident from the above results, that one can grow human primordia, so as to provide differentiation and maturation of organs simulating fetal development in the natural host. In this manner, one may study fetal maturation in a convenient in vivo container (host), where nutrients are continually provided while waste products removed. There appears to be very little interference in the maturation and differentiation of xenogeneic, e.g., human tissue, by the foreign host products, and the developing tissue can be studied as to its response to agents.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of growing bone primordium from a human host, said method comprising:

implanting said bone primordium into a scid/scid mouse host at a site capable of vascularization of said primordium; and growing said mouse host, wherein said bone primordium grows to provide an organ having approximately the structure and shape associated with a fetal organ of about the same age.

2. A method of growing primordium from a human host wherein said primordium is bone, said method comprising:

implanting said primordium into a C.B-17 scid/scid mouse host at a site capable of vascularization of said primordium; and growing said mouse host, wherein said primordium grows to provide an organ having approximately the structure and shape associated with a fetal organ of about the same age.

3. A method according to claim 2, including the additional step of introducing human hematopoietic cells into the shaft of said bone.

4. A method according to claim 3, wherein said hematopoietic cells comprise stem cells.

5. A method according to claim 2, wherein said mouse host is at least partially irradiated.

6. A method according to claim 1, wherein said organ grows for at least about three months.

7. A method for determining the effect of an agent on bone primordium growth, said method comprising:

subjecting a mouse host comprising human bone primordium tissue to said agent; and determining the effect of said agent on said bone primordium growth as compared to said growth in the absence of said agent;

wherein said host is produced by the method comprising:

implanting said bone primordium into a acid/acid mouse host at a site capable of vascularization of said bone primordium; and growing said mouse host, wherein said bone primordium grows to provide an organ having approximately the structure and shape associated with a fetal organ of about the same age.

8. A method for determining the effect of an agent on hematopoietic cell growth, said method comprising:

subjecting a mouse host comprising human hematopoietic cells present as part of solid tissue to said agent; and determining the effect of said agent on said hematopoietic cells as compared to said hematopoietic cells in the absence of said agent;

wherein said host is produced by the method comprising:

implanting human bone primordium into a C.B-17 scid/scid mouse host at a site capable of vascularization of said bone primordium;

growing said host, wherein said bone primordium grows to provide an organ having approximately the structure and shape associated with a fetal organ of about the same age;

ablating endogenous bone marrow in said bone; and implanting human hematopoietic cells into said bone.

9. A method according to claim 8, wherein said human hematopoietic cells which are implanted comprise stem cells.

* * * * *